US00PP24029P2

(12) United States Plant Patent
Fraser

(10) Patent No.: US PP24,029 P2
(45) Date of Patent: Nov. 12, 2013

(54) ***CORDYLINE* PLANT NAMED 'CAN CAN'**

(50) Latin Name: *Cordyline australis*
Varietal Denomination: Can Can

(76) Inventor: Peter Fraser, Waikato (NZ)

( * ) Notice: Subject to any disclaimer, the term of this patent is extended or adjusted under 35 U.S.C. 154(b) by 140 days.

(21) Appl. No.: 13/200,678

(22) Filed: Sep. 28, 2011

(51) Int. Cl.
*A01H 5/00* (2006.01)

(52) U.S. Cl.
USPC ..... Plt./383

(58) Field of Classification Search
USPC ..... Plt./373, 263.1, 383
See application file for complete search history.

*Primary Examiner* — Howard Locker

(57) ABSTRACT

A new cultivar of *Cordyline* plant named 'Can Can' that is characterized by a compact habit and linear shaped variegated leaves that are grey-green with pink margins when young and mature to green with yellow margins.

1 Drawing Sheet

Botanical classification: *Cordyline australis*.
Variety denomination: 'Can Can'.

BACKGROUND OF THE INVENTION

The present invention relates to a new and distinct cultivar of *Cordyline australis* and is hereinafter referred to by the cultivar name 'Can Can'. The new cultivar was discovered by the inventor in a cultivated area of Kihikihi, Waikato, New Zealand in 2007. The new cultivar was discovered as a single plant in a bed of unidentified *Cordyline australis* cultivars. The exact parent plants are unknown.

The new cultivar was first asexually propagated by tissue culture in Auckland, New Zealand in 2007. Since that time, under careful observation, the unique characteristics of the new cultivar have been uniform, stable and reproduced true to type by tissue culture in successive generations of asexual reproduction.

SUMMARY OF THE INVENTION

The new *Cordyline* cultivar 'Can Can' is distinguished from other known varieties of *Cordyline*, by the following characteristics:

1. *Cordyline* 'Can Can' exhibits a compact habit.
2. *Cordyline* 'Can Can' exhibits linear shaped leaves
3. *Cordyline* 'Can Can' exhibits young leaves that are grey-green with pink margins and mature leaves that are green with yellow margins.

The closest comparison cultivar is *Cordyline* 'Abertii' (not patented). 'Can Can' is distinguishable from 'Albertii' in having a shorter height, young leaves that are grey-green with pink margins and mature leaves that are green with yellow margins. The leaves of 'Albertii' are green with yellow margins.

BRIEF DESCRIPTION OF THE DRAWINGS

The accompanying color photograph illustrates the distinguishing characteristics of the new cultivar 'Can Can'. The photograph shows an overall view of a 2 year old plant. All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Cordyline* cultivar named 'Can Can'. Data was collected in Kihikihi, Waikato, New Zealand from 2 year old plants. The plants were grown outdoors in 2.5 liter containers under 50 percent shade house cover. The time of year was late Winter in the Southern Hemisphere. Phenotypic differences may be observed with variations in environmental, climatic, and cultural conditions, without however, any difference in genotype. Color determinations are in accordance with The 2001 Royal Horticultural Society Colour Chart except where general color terms of ordinary dictionary significance are used. The growing requirements are similar to the species and no disease problems have been observed.

Botanical classification: *Cordyline australis* 'Can Can'.
Common name: Cabbage Tree.
Parentage: The exact parent plants of 'Can Can' are unknown.
Type: Ornamental perennial.
Growth rate: Approximately 8 cm. per month.
Habit: Upright, arching.
Height: 2.0 m. in height.
Spread: 1.5 m. in width.
Low temperature tolerance: −5 degrees Centigrade.
High temperature tolerance: 40 degrees Centigrade.
Propagation method: Tissue Culture.
Vigor: Moderate.
Root system: Fine and fibrous.
Stem:
- *Texture*.—Smooth.
- *Dimensions*.—Average 3.5 cm. in diameter and 7 cm. in length.
- *Color*.—177B.

Foliage:
- *Orientation*.—Initially erect than outwardly arching.
- *Average number of leaves per plant*.—44.
- *Compound or single*.—Single.
- *Leaf shape*.—Linear.
- *Leaf dimensions*.—Average 50 cm. in length and 20 mm. in width.

*Leaf apex*.—Acute.
*Leaf base*.—Attenuate.
*Leaf margins*.—Entire.
*Leaf texture*.—Upper and lower surfaces: Smooth.
*Leaf substance*.—Leathery.
*Leaf color of young leaves* (upper surface).—197A with margins N57B.
*Leaf color of young leaves* (lower surface).—197B with margins 43D.
*Leaf color of mature leaves* (upper surface).—137B with margins 12B.
*Leaf color of mature leaves* (lower surface).—133B with margins 12D.
*Venation pattern*.—Parallel.
*Petiole*.—Absent.
*Pinching*.—Removal of young plant tips is not required.
*Flower production*.—'Can Can' has not produced any flowers to date.
*Disease and pest resistance*.—No disease problems have been observed.

The invention claimed is:

1. A new and distinct variety of *Cordyline* plant named 'Can Can' as described and illustrated.

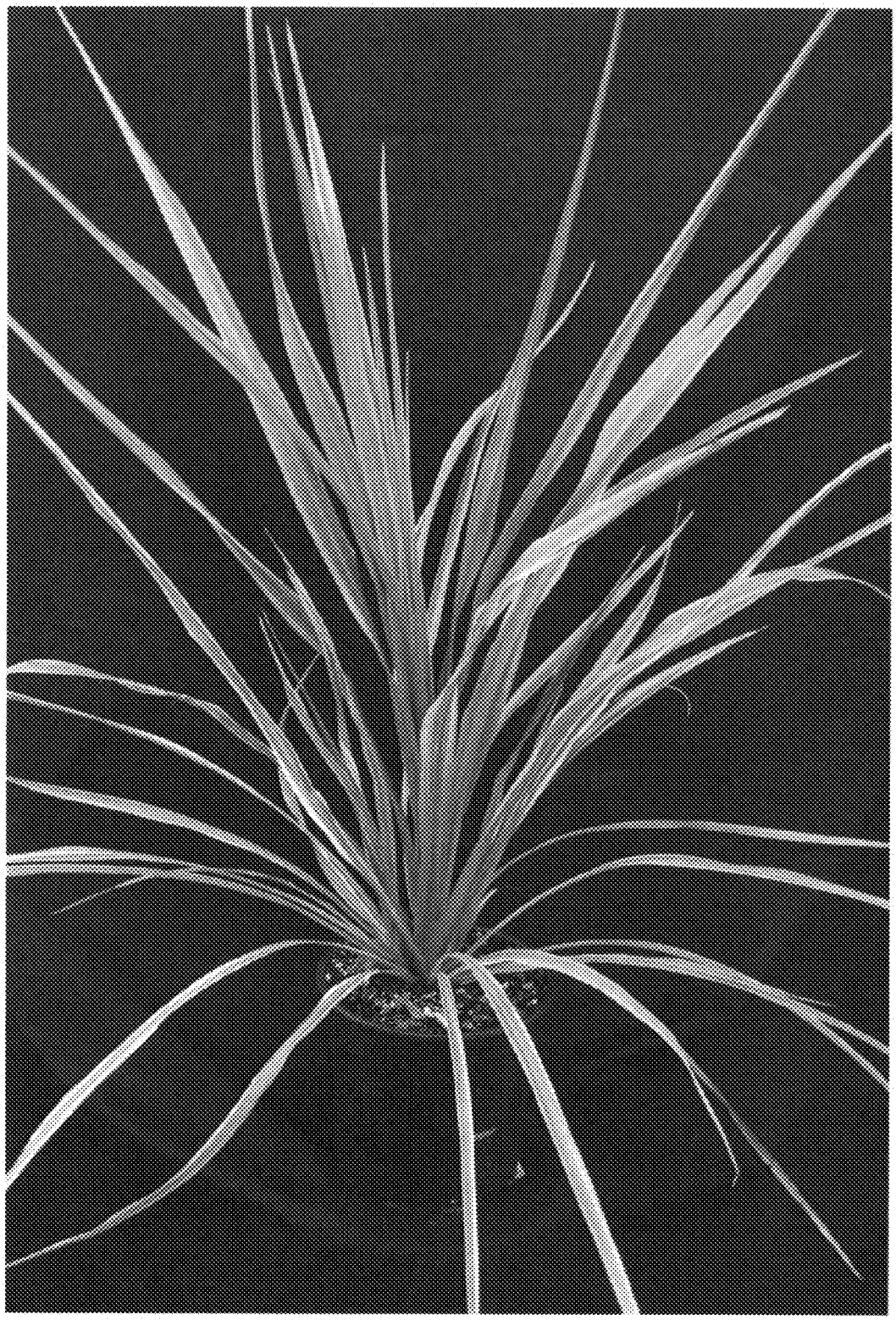

* * * * *